(12) United States Patent
Pham et al.

(10) Patent No.: US 10,687,752 B2
(45) Date of Patent: Jun. 23, 2020

(54) DETECTING UNMEASURABLE LOADS USING HEART RATE AND WORK RATE

(71) Applicant: Apple Inc., Cupertino, CA (US)

(72) Inventors: Hung A. Pham, Oakland, CA (US); Karthik Jayaraman Raghuram, Santa Clara, CA (US); Hengliang Zhang, Cupertino, CA (US); Edith Merle Arnold, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 136 days.

(21) Appl. No.: 15/689,113

(22) Filed: Aug. 29, 2017

(65) Prior Publication Data

US 2018/0055439 A1    Mar. 1, 2018

Related U.S. Application Data

(60) Provisional application No. 62/380,623, filed on Aug. 29, 2016.

(51) Int. Cl.
*A61B 5/00* (2006.01)
*A61B 5/22* (2006.01)
(Continued)

(52) U.S. Cl.
CPC .............. *A61B 5/222* (2013.01); *A61B 5/01* (2013.01); *A61B 5/0205* (2013.01);
(Continued)

(58) Field of Classification Search
CPC ... A61B 5/1118; A61B 5/1123; A61B 5/0205; A61B 5/02416; A61B 5/02438;
(Continued)

(56) References Cited

U.S. PATENT DOCUMENTS

| | | | |
|---|---|---|---|
| 4,566,461 | A | 1/1986 | Lubell et al. |
| 5,158,093 | A | 10/1992 | Shvartz et al. |

(Continued)

FOREIGN PATENT DOCUMENTS

| | | |
|---|---|---|
| GB | 2465824 | 6/2010 |
| IN | 259/KOL/2015 | 12/2015 |

(Continued)

OTHER PUBLICATIONS

Your Fitness FAQ, Why is it important to warm up and cool down in a workout?, 2012, Web, Retrieved from: http://www.yourfitnessfaq.com/whyisitimportanttowarmupandcooldowninaworkout.html.

(Continued)

*Primary Examiner* — Max F Hindenburg
(74) *Attorney, Agent, or Firm* — DLA Piper LLP

(57) ABSTRACT

A method and a system for determining an energy expenditure of a user by detecting unmeasurable loads using heart rate and work rate are described. Time-stamped heart rate data and work rate data can be collected by one or more sensing modules. A processor circuit can calculate a heart rate-based energy expenditure and a work rate-based energy expenditure. The processor circuit can output a hybrid energy expenditure based on a heart rate confidence parameter, an exercise type, a fraction of heart rate reserve, and a hear rate-based metabolic equivalents of task.

14 Claims, 10 Drawing Sheets

(51) Int. Cl.
  *A61B 5/01* (2006.01)
  *A61B 5/0205* (2006.01)
  *A61B 5/11* (2006.01)
  *A61B 5/024* (2006.01)

(52) U.S. Cl.
  CPC ...... *A61B 5/02416* (2013.01); *A61B 5/02438* (2013.01); *A61B 5/1107* (2013.01); *A61B 5/1118* (2013.01); *A61B 5/1123* (2013.01); *A61B 5/0002* (2013.01); *A61B 5/681* (2013.01); *A61B 2505/09* (2013.01); *A61B 2560/0209* (2013.01); *A61B 2562/0219* (2013.01)

(58) Field of Classification Search
  CPC ....... A61B 5/4866; A61B 5/01; A61B 5/1107; A61B 5/222; A61B 5/681
  See application file for complete search history.

(56) References Cited

U.S. PATENT DOCUMENTS

| | | | |
|---|---|---|---|
| 5,663,897 | A | 9/1997 | Geiser |
| 6,013,008 | A | 1/2000 | Fukushima |
| 6,059,724 | A | 5/2000 | Campell et al. |
| 6,582,380 | B2 | 6/2003 | Kazlausky et al. |
| 6,687,535 | B2 | 2/2004 | Hautala et al. |
| 6,837,827 | B1 | 1/2005 | Lee et al. |
| 6,868,338 | B1 | 3/2005 | Elliott |
| 7,254,516 | B2 | 8/2007 | Case, Jr. et al. |
| 7,311,675 | B2 | 12/2007 | Peifer et al. |
| 7,467,060 | B2 | 12/2008 | Kulach et al. |
| 7,534,206 | B1 | 5/2009 | Lovitt et al. |
| 7,690,556 | B1 | 4/2010 | Kahn et al. |
| 7,771,320 | B2 | 8/2010 | Riley et al. |
| 7,805,149 | B2 | 9/2010 | Werner et al. |
| 7,841,967 | B1 | 11/2010 | Kahn et al. |
| 8,290,480 | B2 | 10/2012 | Abramson et al. |
| 8,483,775 | B2 | 7/2013 | Buck et al. |
| 8,589,174 | B2 | 11/2013 | Nelson et al. |
| 8,892,391 | B2 | 11/2014 | Tu et al. |
| 8,894,576 | B2 | 11/2014 | Alwan et al. |
| 8,911,329 | B2 | 12/2014 | Lin et al. |
| 9,413,871 | B2 | 8/2016 | Nixon et al. |
| 9,526,430 | B2 | 12/2016 | Srinivas et al. |
| 9,788,794 | B2 | 10/2017 | Le Boeuf et al. |
| 10,188,347 | B2 * | 1/2019 | Self ............................ G06F 19/00 |
| 10,206,627 | B2 | 2/2019 | Le Boeuf et al. |
| 10,219,708 | B2 * | 3/2019 | Altini ................... A61B 5/1118 |
| 10,292,606 | B2 * | 5/2019 | Wisbey .............. A61B 5/02405 |
| 2001/0022828 | A1 | 9/2001 | Pyles |
| 2002/0019585 | A1 | 2/2002 | Dickinson |
| 2003/0032460 | A1 | 2/2003 | Cannon et al. |
| 2003/0138763 | A1 | 7/2003 | Roncalez et al. |
| 2004/0064061 | A1 | 4/2004 | Nissila |
| 2005/0107723 | A1 | 5/2005 | Wehman et al. |
| 2006/0064277 | A1 | 3/2006 | Jung et al. |
| 2006/0136173 | A1 | 6/2006 | Case et al. |
| 2006/0190217 | A1 | 8/2006 | Lee et al. |
| 2006/0217231 | A1 | 9/2006 | Parks et al. |
| 2007/0100666 | A1 | 5/2007 | Stivoric et al. |
| 2007/0150229 | A1 | 6/2007 | Fujiwara |
| 2007/0219059 | A1 | 9/2007 | Schwartz et al. |
| 2007/0275825 | A1 | 11/2007 | O'Brien |
| 2007/0276271 | A1 | 11/2007 | Chan |
| 2008/0096726 | A1 | 4/2008 | Riley et al. |
| 2008/0214360 | A1 | 9/2008 | Stirling et al. |
| 2009/0009320 | A1 | 1/2009 | O'Connor et al. |
| 2009/0024332 | A1 | 1/2009 | Karlov et al. |
| 2009/0043531 | A1 | 2/2009 | Kahn et al. |
| 2009/0063099 | A1 | 3/2009 | Counts et al. |
| 2010/0030350 | A1 | 2/2010 | House et al. |
| 2010/0130890 | A1 | 5/2010 | Matsumura et al. |
| 2010/0184564 | A1 | 7/2010 | Molyneux et al. |
| 2010/0204952 | A1 | 8/2010 | Irlam et al. |
| 2010/0210953 | A1 | 8/2010 | Sholder et al. |
| 2010/0210975 | A1 | 8/2010 | Anthony, III et al. |
| 2010/0217099 | A1 | 8/2010 | Leboeuf et al. |
| 2010/0274102 | A1 | 10/2010 | Teixeira |
| 2010/0298656 | A1 | 11/2010 | Mccombie et al. |
| 2011/0040193 | A1 | 2/2011 | Seppanen et al. |
| 2011/0054359 | A1 | 3/2011 | Sazonov et al. |
| 2011/0082008 | A1 | 4/2011 | Cheung et al. |
| 2011/0131012 | A1 | 6/2011 | Czaja et al. |
| 2011/0152695 | A1 | 6/2011 | Granqvist et al. |
| 2011/0195707 | A1 | 8/2011 | Faerber et al. |
| 2011/0238485 | A1 | 9/2011 | Haumont et al. |
| 2011/0301436 | A1 | 12/2011 | Teixeira |
| 2012/0083715 | A1 | 4/2012 | Yuen et al. |
| 2012/0172677 | A1 | 7/2012 | Logan et al. |
| 2012/0238832 | A1 | 9/2012 | Jang et al. |
| 2012/0296455 | A1 | 11/2012 | Ohnemus et al. |
| 2012/0322621 | A1 | 12/2012 | Bingham et al. |
| 2013/0023739 | A1 | 1/2013 | Russel |
| 2013/0041590 | A1 | 2/2013 | Burich et al. |
| 2013/0053990 | A1 | 2/2013 | Ackland |
| 2013/0096943 | A1 | 4/2013 | Carey et al. |
| 2013/0158686 | A1 | 6/2013 | Zhang et al. |
| 2013/0178335 | A1 | 7/2013 | Lin et al. |
| 2013/0197377 | A1 | 8/2013 | Takahiko et al. |
| 2013/0218053 | A1 | 8/2013 | Kaiser et al. |
| 2013/0267794 | A1 | 10/2013 | Fernstrom et al. |
| 2014/0073486 | A1 | 3/2014 | Ahmed et al. |
| 2014/0087708 | A1 | 3/2014 | Kalita et al. |
| 2014/0088444 | A1 | 3/2014 | Saalasti et al. |
| 2014/0107932 | A1 | 4/2014 | Luna |
| 2014/0109390 | A1 | 4/2014 | Manning |
| 2014/0121471 | A1 | 5/2014 | Walker |
| 2014/0167973 | A1 | 6/2014 | Letchner et al. |
| 2014/0172238 | A1 | 6/2014 | Craine |
| 2014/0197946 | A1 | 7/2014 | Park et al. |
| 2014/0200906 | A1 | 7/2014 | Bentley et al. |
| 2014/0207264 | A1 | 7/2014 | Quy |
| 2014/0213920 | A1 | 7/2014 | Lee et al. |
| 2014/0221854 | A1 | 8/2014 | Wai |
| 2014/0228649 | A1 | 8/2014 | Rayner et al. |
| 2014/0244071 | A1 | 8/2014 | Czaja et al. |
| 2014/0266789 | A1 | 9/2014 | Matus |
| 2014/0276127 | A1 | 9/2014 | Ferdosi et al. |
| 2014/0278139 | A1 | 9/2014 | Hong et al. |
| 2014/0278229 | A1 | 9/2014 | Hong et al. |
| 2014/0316305 | A1 | 10/2014 | Venkatraman et al. |
| 2014/0348367 | A1 | 11/2014 | Vavrus et al. |
| 2015/0087929 | A1 | 3/2015 | Rapoport et al. |
| 2015/0088006 | A1 | 3/2015 | Rapoport et al. |
| 2015/0100141 | A1 | 4/2015 | Hughes |
| 2015/0119728 | A1 | 4/2015 | Blackadar et al. |
| 2015/0148632 | A1 | 5/2015 | Benaron |
| 2015/0250417 | A1 | 9/2015 | Cheng et al. |
| 2015/0256689 | A1 | 9/2015 | Erkkila et al. |
| 2015/0260514 | A1 | 9/2015 | Menelas et al. |
| 2015/0327804 | A1 | 11/2015 | Lefever et al. |
| 2015/0328523 | A1 | 11/2015 | Heling et al. |
| 2015/0338926 | A1 | 11/2015 | Park et al. |
| 2015/0345985 | A1 | 12/2015 | Fung et al. |
| 2015/0357948 | A1 | 12/2015 | Goldstein |
| 2015/0374240 | A1 | 12/2015 | Lee |
| 2016/0021238 | A1 | 1/2016 | Abramson et al. |
| 2016/0057372 | A1 | 3/2016 | Raghuram et al. |
| 2016/0058302 | A1 | 3/2016 | Raghuram et al. |
| 2016/0058329 | A1 | 3/2016 | Srinivas |
| 2016/0058332 | A1 | 3/2016 | Tan et al. |
| 2016/0058333 | A1 | 3/2016 | Arnold et al. |
| 2016/0058356 | A1 | 3/2016 | Raghuram et al. |
| 2016/0058370 | A1 | 3/2016 | Raghuram et al. |
| 2016/0058371 | A1 | 3/2016 | Singh Alvarado et al. |
| 2016/0058372 | A1 | 3/2016 | Raghuram et al. |
| 2016/0059079 | A1 | 3/2016 | Watterson |
| 2016/0084869 | A1 | 3/2016 | Yuen et al. |
| 2016/0166178 | A1 | 6/2016 | Fuss et al. |
| 2016/0170998 | A1 | 6/2016 | Frank et al. |
| 2016/0206248 | A1 | 7/2016 | Sartor et al. |
| 2016/0256058 | A1 | 9/2016 | Pham et al. |
| 2016/0269572 | A1 | 9/2016 | Erkkila et al. |

(56) References Cited

U.S. PATENT DOCUMENTS

| | | | |
|---|---|---|---|
| 2016/0287177 | A1 | 10/2016 | Huppert et al. |
| 2016/0361020 | A1 | 12/2016 | LeBoeuf et al. |
| 2016/0363449 | A1 | 12/2016 | Metzler et al. |
| 2016/0374614 | A1 | 12/2016 | Cavallaro et al. |
| 2017/0007166 | A1 | 1/2017 | Roover et al. |
| 2017/0061817 | A1 | 3/2017 | Mettler May |
| 2017/0074897 | A1 | 3/2017 | Mermel et al. |
| 2017/0082649 | A1 | 3/2017 | Tu et al. |
| 2017/0094450 | A1 | 3/2017 | Tu et al. |
| 2017/0111768 | A1 | 4/2017 | Smith et al. |
| 2017/0188893 | A1 | 7/2017 | Venkatraman et al. |
| 2017/0202486 | A1 | 7/2017 | Martikka et al. |
| 2017/0251972 | A1 | 9/2017 | Jayaraman et al. |
| 2017/0259116 | A1 | 9/2017 | Mestas |
| 2017/0273619 | A1 | 9/2017 | Alvarado et al. |
| 2017/0347885 | A1 | 12/2017 | Tan et al. |
| 2017/0367658 | A1 | 12/2017 | LeBoeuf et al. |
| 2018/0028863 | A1 | 2/2018 | Matsuda |
| 2018/0049694 | A1 | 2/2018 | Singh Alvarado et al. |
| 2018/0050235 | A1 | 2/2018 | Tan et al. |
| 2018/0055375 | A1 | 3/2018 | Martinez et al. |
| 2018/0056123 | A1 | 3/2018 | Narasimha Rao et al. |
| 2018/0056128 | A1 | 3/2018 | Narasimha Rao et al. |
| 2018/0056129 | A1 | 3/2018 | Narasimha Rao et al. |

FOREIGN PATENT DOCUMENTS

| | | |
|---|---|---|
| JP | 2010-051333 A | 3/2010 |
| JP | 2013-39316 A | 2/2013 |
| JP | 2014-42757 A | 3/2014 |
| JP | 2016-150018 A | 8/2016 |
| JP | 2018-000543 A | 1/2018 |
| JP | 2018-015187 A | 2/2018 |
| WO | 2010090867 | 8/2010 |
| WO | 2011/105914 A1 | 9/2011 |
| WO | 2015/126182 A | 8/2015 |
| WO | 2015/200900 A1 | 12/2015 |
| WO | 2016/044831 A1 | 3/2016 |
| WO | 2016/073620 A1 | 5/2016 |

OTHER PUBLICATIONS

Vella et al, Exercise After-Burn: Research Update, 2005, Web, Retrieved from: http://www.unm.edu/~lkravitz/Article%20folder/epocarticle.html.

Song et al., "Training Activity Recognition Systems Online Using Real-Time Crowdsourcing", University of Rochester Computer Science, UbiCom' 12, Sep. 5-8, 2012 (2 pages).

Rowlands et al., "Assessing Sedentary Behavior with the GENEActiv: Introducing the Sedentary Sphere". Medicine and science in sports and exercise 46.6 (2014): 1235-1247.

Hasson et al., "Accuracy of four resting metabolic rate production equations: Effects of sex, body mass index, age, and race/ethnicity", Journal of Science and Medicine in Sport, 2011, vol. 14, p. 344-351.

Lucas et al., "Mechanisms of orthostatic intolerance following very prolonged exercise", 2008, J Appl Physiol, 105: 213-225.

Kunze et al., "Where am i: Recognizing on-body positions of wearable sensors." Location-and context-awareness. Springer Berlin Heidelberg, 2005. 264-275.

Keytel et al., "Prediction of energy expenditure from heart rate monitoring during submaximal exercise", 2005, Journal of Sports Sciences, 23(3):289-97.

Sabatini, Kalman-filter-based orientation determination using inertial/magnetic sensors: observability analysis and performance evaluation, Sep. 27, 2011, Sensors Nov. 2011, 9182-9206.

Jackson et al., "Prediction of functional aerobic capacity without exercise testing", Medicine and Science in Sports and Exercise, 22(6), 863-870, 1990.

Isaacs et al., "Modeling energy expenditure and oxygen consumption in human exposure models: accounting for fatigue and EPOC", 2008, Journal of Exposure Science and Environmental Epidemiology, 18: 289-298.

Human Kinetics, Aerobic Workout Components, 2011, Web, Retrieved from: http://www.humankinetics.com/excerpts/excerpts/aerobicworkoutcomponentsexcerpt.

Gao et al., "Evaluation of accelerometer based multi-sensor versus single-sensor activity recognition systems." Medical engineering & physics 36.6 (2014): 779-785.

Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.

Chu, "In-Vehicle Driver Detection Using Mobile Phone Sensors", Submitted for Graduation with departmental Distinction in Electrical and Computer Engineering, Apr. 20, 2011, pp. 1-21.

Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Bruce, R.A. et al., "Exercising testing in adult normal subjects and cardiac patients," Pediatrics, vol. 32, No. Suppl., pp. 742-756 (Oct. 1963).

Bruce, R.A. et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

Myers, J. et al., "Exercise Capacity and Mortality Among Men Referred for Exercise Testing," The New England Journal of Medicine, vol. 346, No. 11, pp. 793-801 (Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

(56) References Cited

OTHER PUBLICATIONS

Yamaji, et al., "Relationship Between Heart Rate and Relative Oxygen Intake in Male Subjects Aged 10 to 27 Years", J. Human Ergol., 7:29-39, Jan. 27, 1978.
KINprof, May 31, 2011, Predictive VO2max tests, Web Video, Retrieved from: https://www.youtube.com/watch?v=_9e3HcY1sm8.
PCT International Application No. PCT/US2017/049693, International Search Report dated Aug. 12, 2017, 3 pages.
Novatel, "IMU Error and Their Effects", Novatel Application Notes APN-064 Rev A p. 1-6, Feb. 21, 2014.
International Search Report and Written Opinion received for PCT Patent Application No. PCT/US2018/047290, dated Nov. 8, 2018, 14 pages.
Le, et al., "Sensor-based Training Optimization of a Cyclist Group", Seventh International Conference on Hybrid Intelligent Systems, IEEE 2007, pp. 265-270.
Kyle, Chester R., "Reduction of Wind Resistance and Power Output of Racing Cyclists and Runners Travelling in Groups", Ergonomics, vol. 22, No. 4, 1979, pp. 387-397.
McArdle, W.D. et al., "Exercise Physiology: Nutrition, Energy and Human Performance", Seventh Edition, Lippincott Wiiliams & Wilkins, 2010, Chapters 5-11 and 21, pp. 118-198.

\* cited by examiner

DETECTING UNMEASURABLE LOADS USING HEART RATE AND WORK RATE

CROSS-REFERENCE TO RELATED APPLICATION

This application claims priority to and the benefit of U.S. Provisional Application No. 62/380,623 filed on Aug. 29, 2016, the disclosure of which is incorporated by reference herein in its entirety.

FIELD

The present disclosure relates generally to improving calorie expenditure prediction and tracking and, more particularly, to techniques for determining energy expenditure by detecting unmeasurable loads using heart rate and work rate.

BACKGROUND

When walking or running without any additional loads, calorie burn can be accurately and robustly predicted from mechanics (e.g., gait speed and terrain incline). Speed and incline can be sensed using accelerometer, barometer, and GPS signals. However, if there are any additional loads that cannot be observed with these sensors (such as treadmill incline, a backpack, a heavy stroller, or inefficient movement patterns due to pathology) or if one of these sensors is not available (e.g., a user does not have a barometric sensor or is on an inclined treadmill where elevation is not actually changing with incline) then estimation of calories burn will be inaccurate.

SUMMARY

The present disclosure relates to a method for improving an accuracy of a wearable device while calculating an energy expenditure of a user. In some embodiments, the method can include: determining, by a processor circuit of the wearable device, a start of an exercise session for the user; detecting, by the processor circuit, an exercise type associated with the exercise session wherein the exercise type is walking or running; measuring, by a heart rate sensing module of the wearable device, heart rate data of the user, wherein the heart rate sensing module comprises a photoplethysmogram (PPG) sensor and the PPG sensor is configured to be worn adjacent to the user's skin; applying, by the processor circuit, a first time stamp to the measured heart rate data; collecting, by one or more work rate sensing modules of the wearable device, work rate data of the user; applying, by the processor circuit, a second time stamp to the collected work rate data; calculating, by the processor circuit, a heart rate-based energy expenditure based on the heart rate data measured at the first time stamp; calculating, by the processor circuit, a work rate-based energy expenditure based on the work rate data collected at the second time stamp; determining, by the processor circuit, an energy expenditure of the user based on the calculated heart rate-based energy expenditure and the calculated work rate-based energy expenditure; and outputting the energy expenditure of the user.

In some embodiments, the method can include: determining, by the processor circuit, a heart rate confidence parameter based on the collected measured heart rate data; measuring, by the heart rate sensing module a maximum heart rate and a resting heart rate; calculating, by the processor circuit, a fraction of heart rate reserve (FHR) based on the collected measured heart rate data, the maximum heart rate, and the resting heart rate; and calculating, by the processor circuit, the heart rate-based energy expenditure based on the FHR.

In some embodiments, the method can include: determining the energy expenditure of the user as the calculated work rate-based energy expenditure when the determined heart rate confidence parameter is less than a pre-defined heart rate confidence threshold, the detected exercise type is running and the calculated fraction of heart rate reserve is greater than a pre-defined fraction of heart rate reserve threshold, or the detected exercise type is walking and a heart rate-based metabolic equivalents of task is greater than a pre-defined metabolic equivalents of task threshold; and determining the energy expenditure of the user as the greater of the calculated heart rate-based energy expenditure and the calculated work rate-based energy expenditure when the determined heart rate confidence parameter is greater than or equal to a pre-defined heart rate confidence threshold, the detected exercise type is running and the calculated fraction of heart rate reserve is less than or equal to a pre-defined fraction of heart rate reserve threshold, or the detected exercise type is walking and a heart rate-based metabolic equivalents of task is less than or equal to a pre-defined metabolic equivalents of task threshold.

In some embodiments, the pre-defined metabolic equivalents of task threshold is between 0 and 50.

In some embodiments, the wearable device can received an input from the user indicating a start of an exercise session.

In some embodiments, the one or more work rate sensing module can include a motion sensing module. In some embodiments, the motion sensing module can include at least one of an accelerometer, a gyroscope, a magnetometer, an altimeter, a barometer, or a GPS sensor.

The present disclosure also relates to a system for improving the accuracy of a wearable device while calculating an energy expenditure of a user. In some embodiments, the system can include: a heart rate sensing module configured to measure heart rate data of the user, wherein the heart rate sensing module comprises a photoplethysmogram (PPG) sensor and the PPG sensor is configured to be worn adjacent to the user's skin; one or more work rate sensing modules configured to collect work rate data of the user; and a processor circuit in communication with the heart rate sensing module and the one or more work rate sensing modules. The processor circuit is configured to execute instructions causing the processor circuit to: determine a start of an exercise session for the user; detect an exercise type associated with the exercise session wherein the exercise type is walking or running; apply a first time stamp to the measure heart rate data; apply a second time stamp to the collected work rate data; calculate a heart rate-based energy expenditure based on the heart rate data measured at the first time stamp; calculating a work rate-based energy expenditure based on the work rate data collected at the second time stamp; determine an energy expenditure of the user based on the calculated heart rate-based energy expenditure and the calculated work rate-based energy expenditure; and output the energy expenditure of the user.

Other features and advantages will become apparent from the following detailed description and drawings.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Systems and methods are disclosed herein to determine energy expenditure by detecting unmeasurable loads using heart rate and work rate. As described above, unmeasurable loads, such as added weight or inclines that are not easily measured using position-based techniques, can skew a caloric estimation based on measured heart rate and positional data. To account for the unmeasurable loads, in some embodiments, the number of calories burned as predicted by mechanics, is simultaneously monitored, with heart rate. A dynamic comparison of the calories burned and heart rate can then be used as an indicator of load that is unmeasured by body mechanics. This indicator enables an intelligent selection of mechanics or heart rate based models to maximize accuracy, precision, and robustness of calorie prediction.

Figure 1:
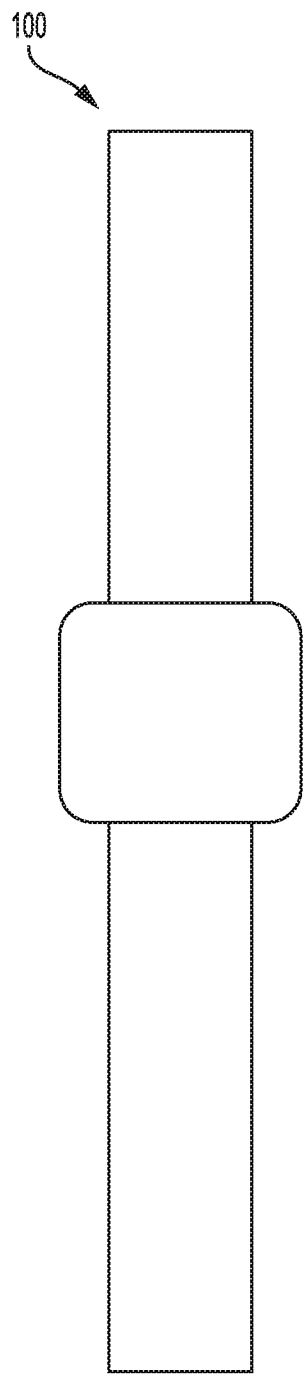
FIG. 1 shows an example of a fitness tracking device 100, according to some embodiments of the present disclosure.

FIG. 1 shows an example of a fitness tracking device 100, according to some embodiments of the present disclosure. In some embodiments, the fitness tracking device 100 may be a wearable device, such as a watch configured to be worn around an individual's wrist. As described in more detail below, the fitness tracking device 100 may be calibrated according to physical attributes of the individual and physical activity by the individual user who is wearing the fitness tracking device 100, including, for example, heart rate statistics.

Figure 2:
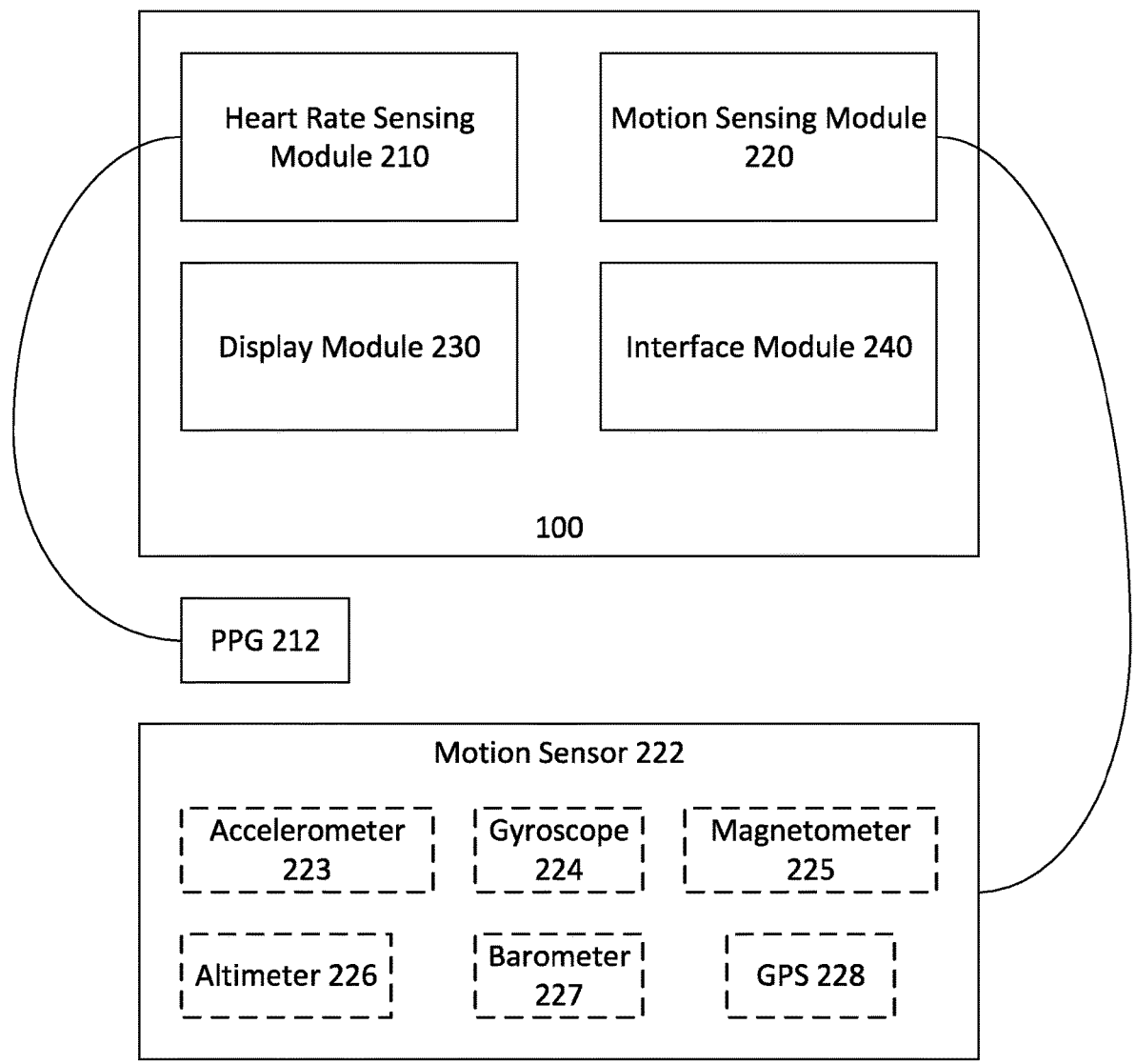
FIG. 2 depicts a block diagram of example components that may be found within the fitness tracking device 100, according to some embodiments of the present disclosure.

FIG. 2 depicts a block diagram of example components that may be found within the fitness tracking device 100, according to some embodiments of the present disclosure. These components may include a heart rate sensing module 210, a motion sensing module 220, a display module 230, and an interface module 240.

The heart rate sensing module 210 may include or may be in communication with a photoplethysmogram "PPG" sensor 212 as previously described. The fitness tracking device 100 can measure an individual's current heart rate from the PPG 212. The heart rate sensor may also be configured to determine a confidence level indicating a relative likelihood of an accuracy of a given heart rate measurement. In other embodiments, a traditional heart rate monitor may be used and may communicate with the fitness tracking device 100 through a near field communication method (e.g., Bluetooth®).

The fitness tracking device 100 may include an LED and a photodiode or the equivalent to obtain a PPG 212. The fitness tracking device 100 may subsequently determine the user's current heart rate based on the PPG data.

To conserve battery power on the fitness tracking device 100, the LED may be a relatively low-power LED, such as a green LED. In some embodiments, to further conserve power on the fitness tracking device 100, the fitness tracking device 100 may be configured to check heart rate at periodic intervals (e.g., once per minute, or once per three minutes). The period for checking heart rate may change dynamically. For example, if the fitness tracking device 100 automatically detects or receives input from the user that the user is engaged in a certain level, intensity, or type of physical activity (e.g., "in session"), the fitness tracking device may check heart rate more frequently (e.g., once per thirty seconds, once per minute, etc.). The fitness tracking device 100 may use, for example, machine learning techniques, battery power monitoring, or physical activity monitoring to balance the frequency of heart rate samples for accurate calorimetry with power optimization.

In addition to the heart rate sensing module 210, the fitness tracking device 100 may also include the motion sensing module 220. The motion sensing module 220 may include one or more motion sensors 222, such as an accelerometer 223 or a gyroscope 224. In some embodiments, the accelerometer 222 may be a three-axis, microelectromechanical system (MEMS) accelerometer 222, and the gyroscope 223 may be a three-axis MEMS gyroscope 223. A microprocessor (not shown) or motion coprocessor (not shown) of the fitness tracking device 100 may receive motion information from the motion sensors 222 of the motion sensing module 220 to track acceleration, rotation, position, or orientation information of the fitness tracking device 100 in six degrees of freedom through three-dimensional space.

In some embodiments, the motion sensing module 220 may include other types of sensors 222 in addition to accelerometers 223 and gyroscopes 224. For example, the motion sensing module 220 may include a magnetometer 225, an altimeter 226, or a barometer 227, or other types of location sensors, such as a GPS sensor 228. A barometer 227 (also referred to herein as a barometric sensor) can detect pressure changes and correlate the detected pressure changes to an altitude.

In some embodiments, the fitness tracking device 100 may take advantage of the knowledge that the heart rate sensing module 210 and the motion sensing module 220 are approximately collocated in space and time to combine data from each module 210 and 220 to improve the accuracy of its calorimetry functionality. Depending on the current activity and a determination of a confidence of current heart rate and motion data, the fitness tracking device 100 may also rely on one of either the heart rate or a motion-derived work rate to estimate energy expenditure more accurately.

The fitness tracking device 100 may also include a display module 230. Display module 230 may be a screen, such as a crystalline (e.g., sapphire) or glass touchscreen, configured to provide output to the user as well as receive input form the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth® (IEEE 802.15) interface, such as Bluetooth® v4.0, also known as "Bluetooth® low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The fitness tracking device 100 may be configured to communicate with a companion device 300 (FIG. 3), such as a smartphone, as described in more detail herein. In some embodiments, the fitness tracking device 100 may be configured to communicate with other external devices, such as a notebook or desktop computer, tablet, headphones, Bluetooth® headset, etc.

The modules described above are examples, and embodiments of the fitness tracking device 100 may include other modules not shown. For example, the fitness tracking device 100 may include one or more microprocessors (not shown) for processing heart rate data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
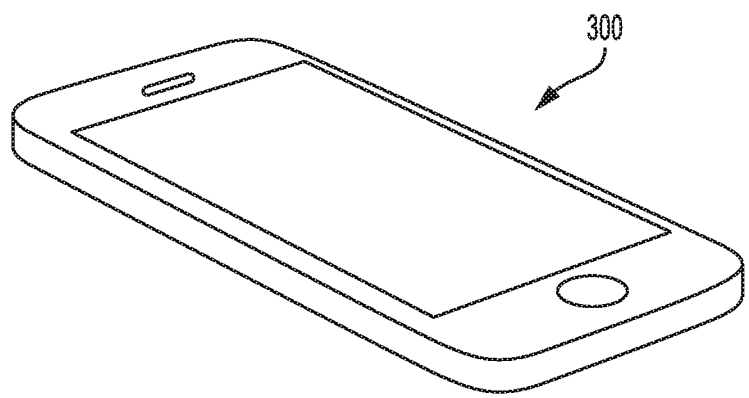
FIG. 3 shows an example of a companion device 300, according to some embodiments of the present disclosure.

FIG. 3 shows an example of a companion device 300, according to some embodiments of the present disclosure. The fitness tracking device 100 may be configured to communicate with the companion device 300 via a wired or wireless communication channel (e.g., Bluetooth®, Wi-Fi, etc.). In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter or barometer, an altimeter or barometer of the companion device 300 may collect altitude or relative altitude information, and the fitness tracking device 100 may receive the altitude or relative altitude information via interface module 240 (FIG. 2) from the companion device 300.

Figure 4:
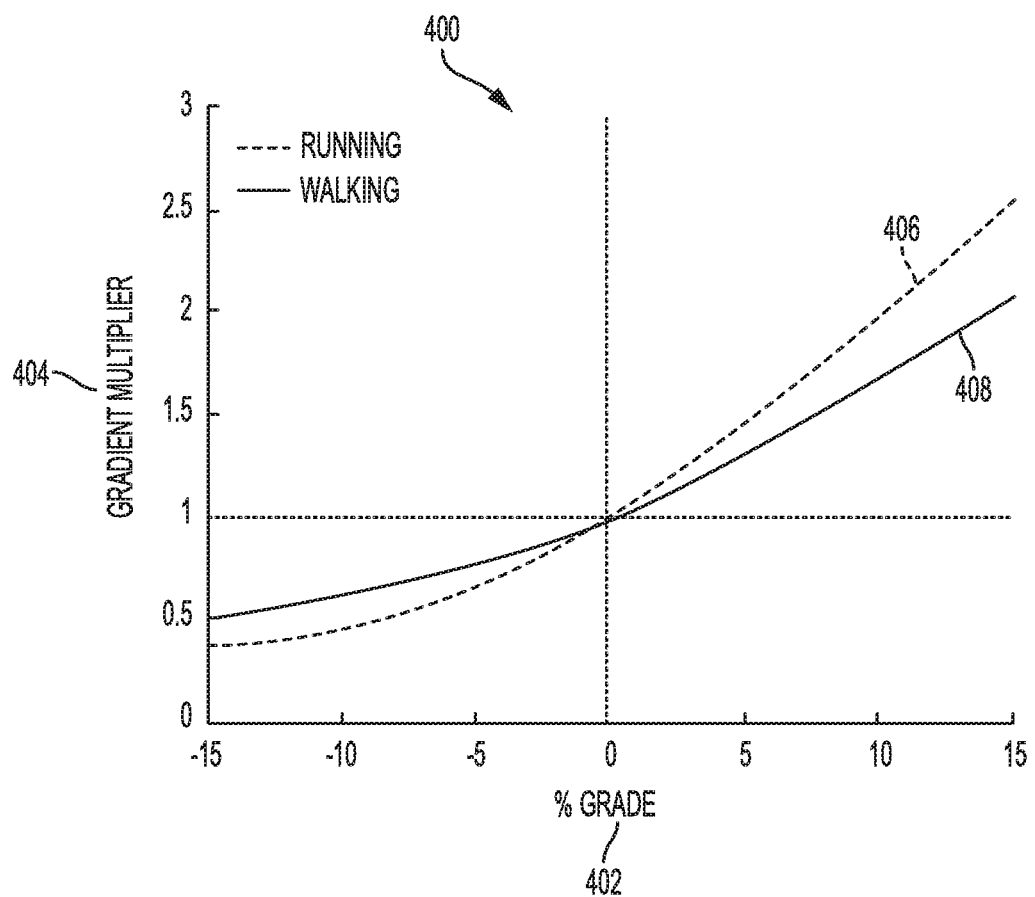
FIG. 4 is a graph showing the effect of incline on the number of calories burned, according to some embodiments of the present disclosure.

FIG. 4 is a graph 400 showing the effect of incline on the number of calories burned, according to some embodiments of the present disclosure. FIG. 4 shows percentage grade 402, gradient multiplier 404, walking curve 406, and a running curve 408.

Percentage (%) grade 402 refers to a level of incline. 0% grade is associated with a flat surface, a negative % grade indicates a downward incline (e.g., a user walking downhill), and a positive % grade indicates an upward incline (e.g., a user walking uphill). The higher the percentage, either positive or negative, reflects a larger incline.

Gradient multiplier 404 indicates a factor by which calorie expenditure increases or decreases due to incline. For example, as shown with respect to both the walking and running curves 406, 408, a positive % grade is associated with a gradient multiplier greater than 1. That is, for a user running or walking on an upward incline, the amount of calories calculated is adjusted by a factor greater than 1.

As shown in FIG. 4, a percentage grade 402 can have a significant effect on calorie estimation. Assuming a perfect work rate estimation, calorie estimation performance degrades at 5% for walking and 1% at running. As described in more detail below, the work rate alone does not capture the amount of work done in the vertical axis, increasingly as a function of grade.

Various techniques exist for determining calorie estimation using measured heart rate or work rate. One technique is to use measured heart rate, maximum heart rate, and resting heart rate to determine a fraction of heart rate reserve (FHR) (referred to herein also as heart rate). Energy expenditure (EE), which is associated with calorie estimation, can be determined based on a calorimetry model using a calorimetry model with a parameterized function of FHR:

$$EE = \dot{V}O_2\text{max} \cdot f(\text{FHR}) \tag{Eq. 1}$$

where $\dot{V}O_2\text{max}$ refers to a maximal oxygen uptake.

Energy expenditure can also be determined as a function of work rate (WR):

$$EE = (A + B \cdot \text{load} \cdot WR)/(\text{efficiency}) \quad \text{(Eq. 2)}$$

where load refers to a resistance associated with exercise, and efficiency refers to a ratio of work output to work input during exercise. The values "A" and "B" can be fixed or otherwise determined. For example, A and B can both be obtained using statistical fits given a measured EE and a load. The load term might take the form of sin(\theta) where \theta corresponds to an inclination angle. The efficiency term is often bundled on an average into A and B across the fit data. In some embodiments, there is a dynamic efficiency parameter that can be estimated as the ration of HR estimated calories to the work rate estimated calories under nominal load. Another expression of energy expenditure is metabolic rate. Metabolic rate may be expressed in Metabolic Equivalents of Task, or METs. METs indicates how many calories a "typical" individual burns per unit of body mass per unit of time. Calculating energy expenditure and METs is further described in U.S. application Ser. No. 15/061,653, filed on Mar. 23, 2016 and U.S. application Ser. No. 15/466,397, filed on Mar. 22, 2017, the contents of which are incorporated herein in their entirety.

Figure 5:
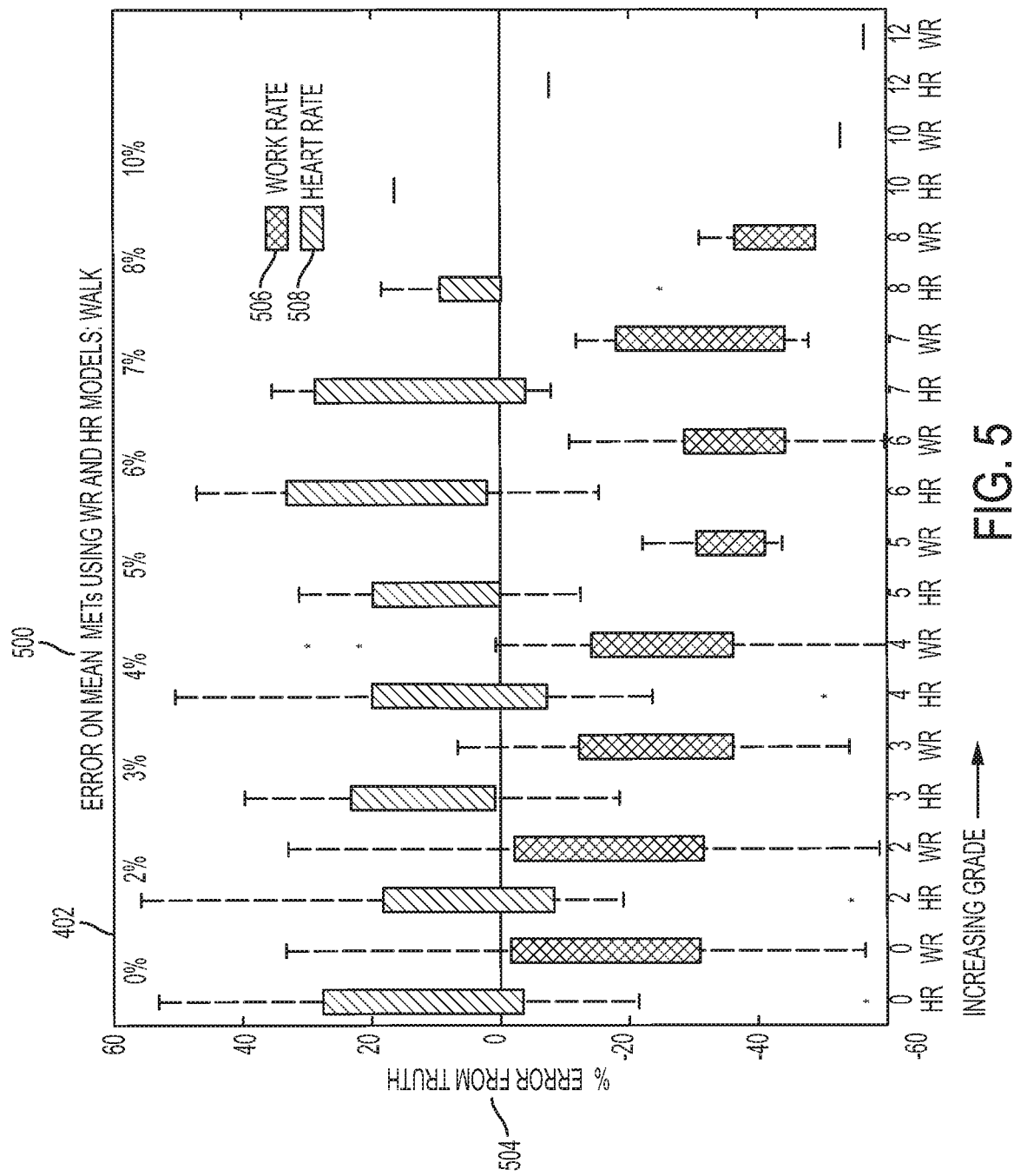
FIG. 5 is a graph 500 showing an error on mean METs using work rate and heart rate models versus grade for 65 users participating in a walking experiment, according to some embodiments of the present disclosure.

FIG. 5 is a graph 500 showing an error on mean METs using work rate and heart rate models versus grade for 65 users participating in a walking experiment, according to some embodiments of the present disclosure. FIG. 5 shows a percentage grade 402, a percentage error from an actual number of METs expended during the experiment 504, work rate-METs range 506, and heart rate-METs range 508.

For the experiment used to generate the data in FIG. 5, 70 subjects participated in a walking experiment. The experiment was conducted in three 5-minute segments, with speed adjustments permitted. 65 of the 70 subjects had complete walking data, with data sparser at grades 6% and higher. Complete walking data here refers to data with speed, grade, heart rate and measured EE.

For the sample of 65 subjects, a mean and standard deviation of a percentage error of each of a work rate-based METs calculation and heart rate-based METs calculation from an actual number of METs expended during the experiment 504 was calculated. The mean and two standard deviations of error from the actual (also referred to herein as real) METs expended is shown for each of a work rate-METs range 506 and a heart rate-METs range 508. As shown in FIG. 5, the higher the percentage grade, the less reliable the work rate-based calorie expenditure estimate. The errors are computed as a percentage of the actual EE from a metabolic cart.

Figure 6:
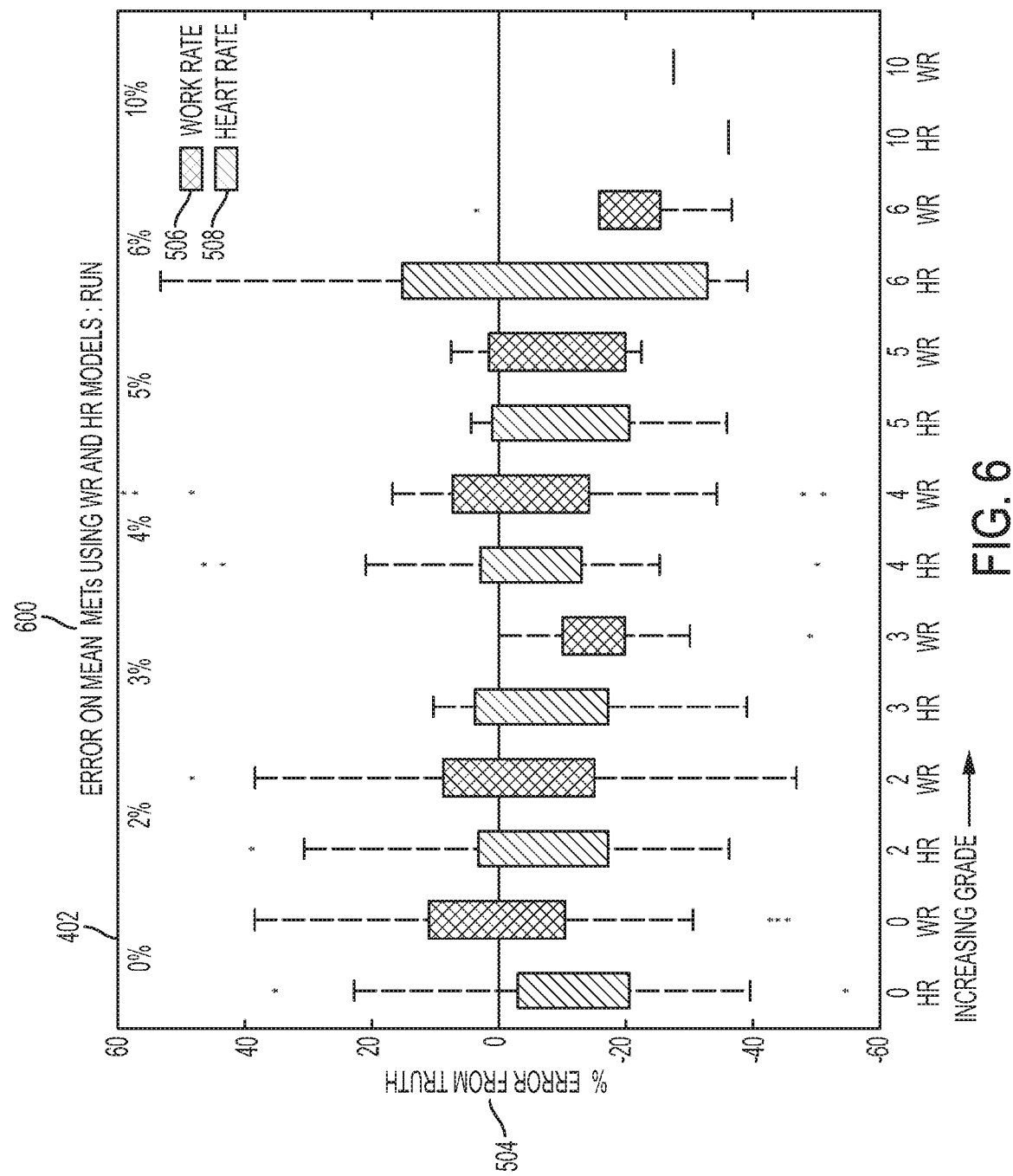
FIG. 6 is a graph 600 showing an error on mean METs using work rate and heart rate models versus grade for 55 users participating in a running experiment, according to some embodiments of the present disclosure.

FIG. 6 is a graph 600 showing an error on mean METs using work rate and heart rate models versus grade for 55 users participating in a running experiment, according to some embodiments of the present disclosure. FIG. 6 shows a percentage grade 402, a percentage error from an actual number of METs expended during the experiment 504, work rate-METs range 506, and heart rate-METs range 508.

For the experiment used to generate the data in FIG. 6, 62 subjects participated in a running experiment. The experiment was conducted in three 5-minute segments, with speed adjustments permitted. 55 of the 62 subjects had complete running data, with data sparser at grades 6% and higher. Complete running data here refers to data with speed, grade, heart rate and measured EE.

For the sample of 55 subjects, a mean and standard deviation of a percentage error of each of a work rate-based METs calculation and heart rate-based METs calculation from an actual number of METs expended during the experiment 504 was calculated. The mean and two standard deviations of error from the actual (also referred to herein as real) METs expended is shown for each of a work rate-METs range 506 and a heart rate-METs range 508. As shown in FIG. 6, the work rate-METs ranges 506 and heart rate-METs ranges 508 are more accurate for running than for walking.

Figure 7:
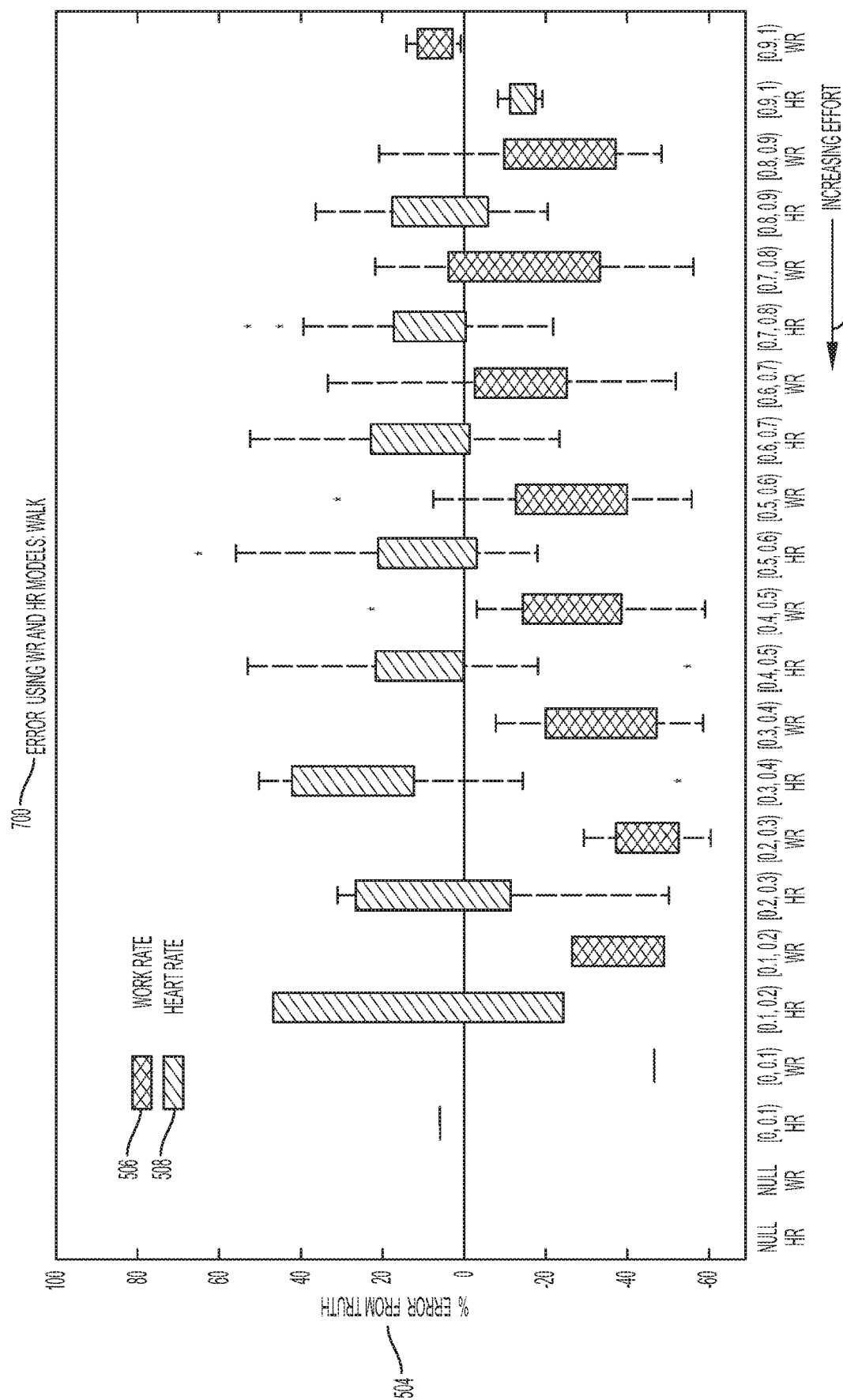
FIG. 7 is a graph 700 showing an error on mean METs using work rate and heart rate models versus effort for 65 users participating in a walking experiment, according to some embodiments of the present disclosure.

FIG. 7 is a graph 700 showing an error on mean METs using work rate and heart rate models versus effort for 65 users participating in a walking experiment, according to some embodiments of the present disclosure. FIG. 7 shows effort 702, a percentage error from an actual number of METs expended during the experiment 504, work rate range 506, and heart rate range 508.

Effort 702 refers to an observed user exertion level such as FHR (fractional heart rate reserve). As shown in FIG. 7, a percentage error from an actual number of METs expended during the experiment 504 associated with heart rate-METs ranges 508 is generally over biased with increasing effort 702. The percentage error from an actual number of METs expended during the experiment 504 associated with work rate-METs ranges 506 is generally under biased with increasing effort 702.

Figure 8:
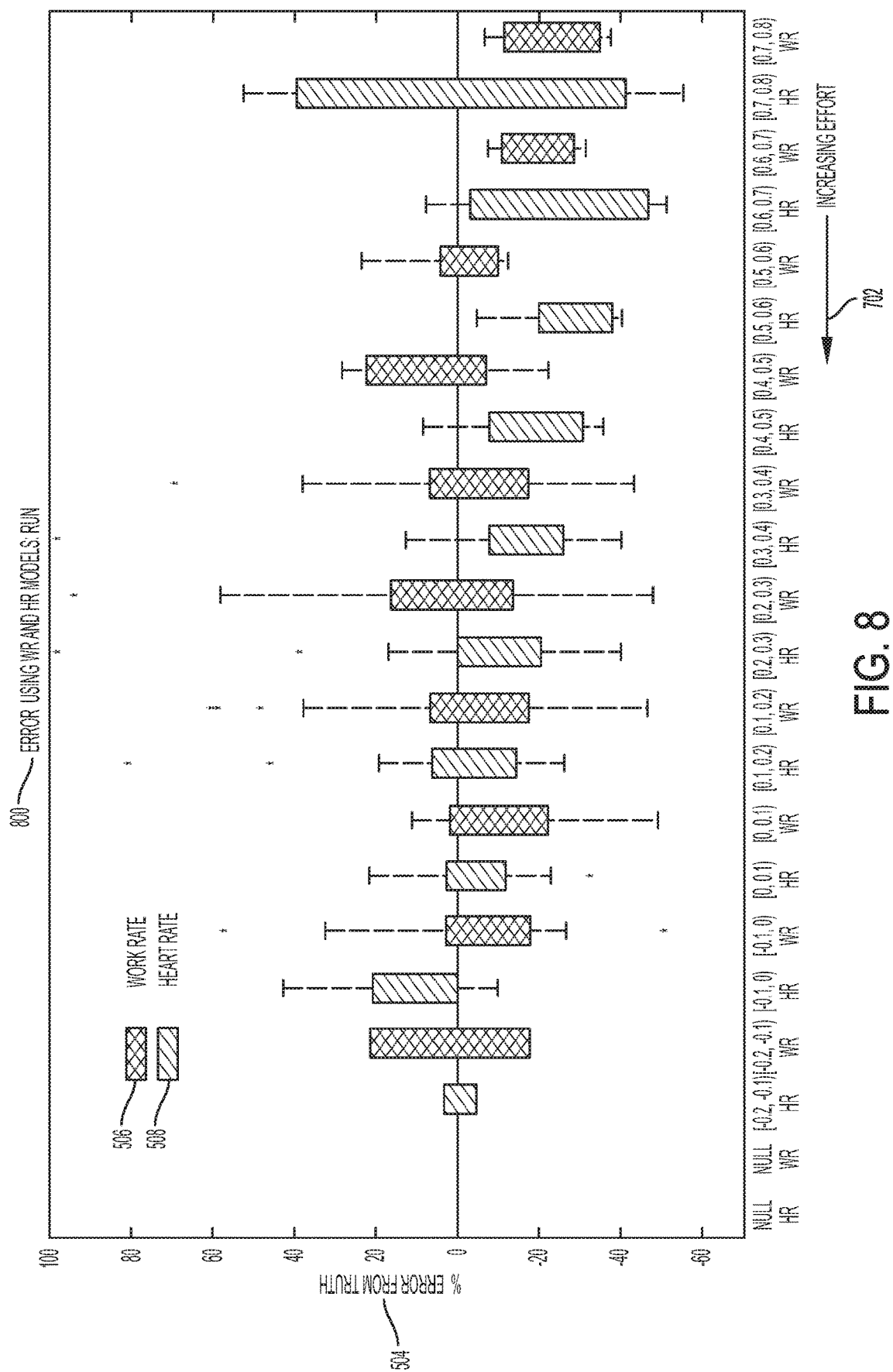
FIG. 8 is a graph 800 showing an error on mean METs using work rate and heart rate models versus effort for 65 users participating in a running experiment, according to some embodiments of the present disclosure.

FIG. 8 is a graph 800 showing an error on mean METs using work rate and heart rate models versus effort for 65 users participating in a running experiment, according to some embodiments of the present disclosure. FIG. 8 shows effort 702, a percentage error from an actual number of METs expended during the experiment 504, work rate-METs range 506, and heart rate-METs range 508.

As shown in FIG. 8, work rate-METs 506 appear to more accurate than heart rate-METs 508 at lower effort levels 702. For runners, work rate-METs 506 and heart rate-METs 508 appear to be similarly accurate.

As shown in FIGS. 5-8, computing METs using only heart rate or work rate measurements does not accurately reflect actual METs when an undetectable load or incline is present. A solution is needed that makes adjustments based on incline, load, and/or effort to gain an accurate calorie determination.

Figure 9:
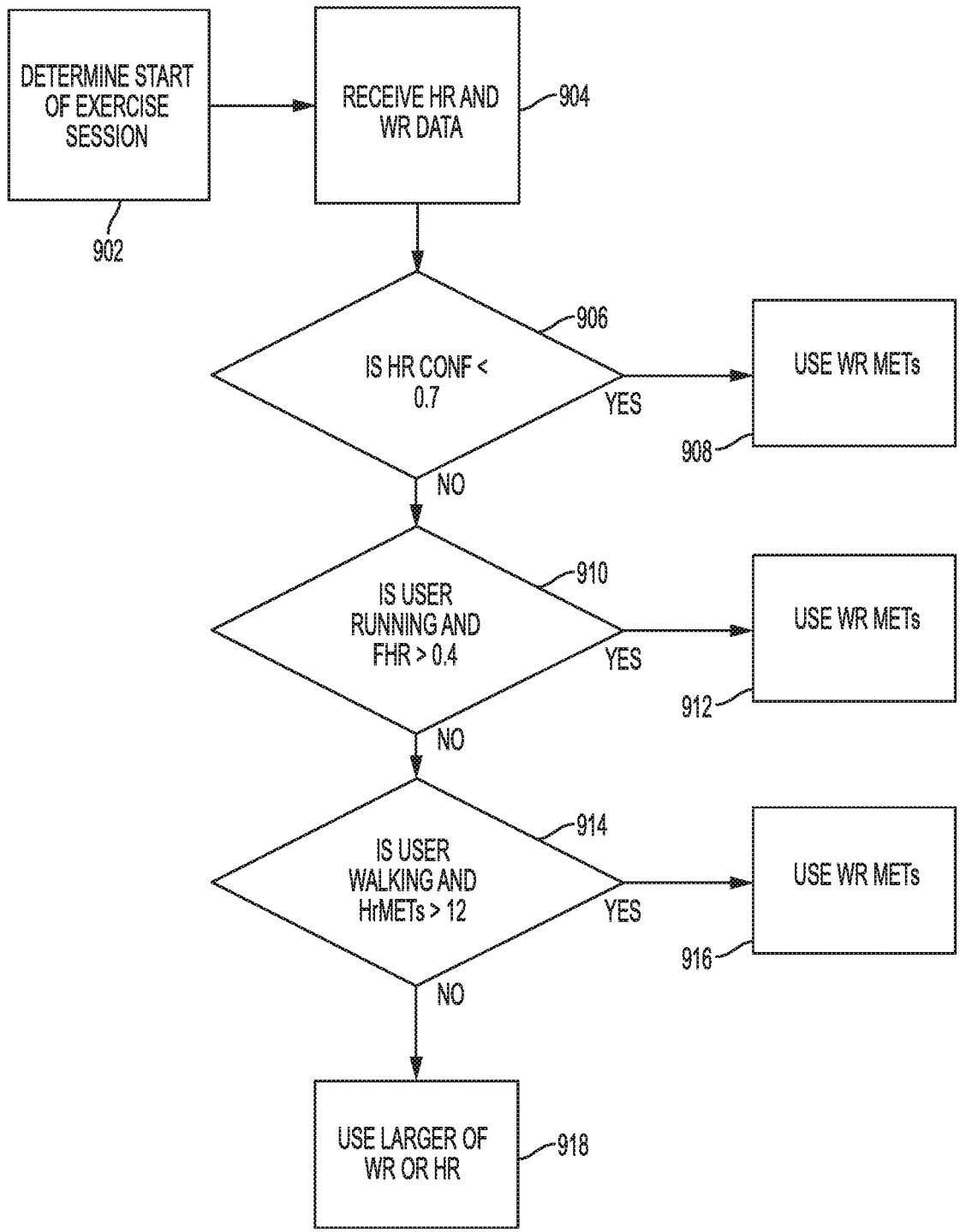
FIG. 9 is a flowchart showing a hybrid algorithm, according to some embodiments of the present disclosure.

FIG. 9 is a flowchart showing a hybrid algorithm, according to some embodiments of the present disclosure. As shown and described above with respect to FIGS. 5-8, work rate- and heart rate-based METs calculations display certain patterns for different combinations of effort, grade, and type of physical activity. As such, based on the observations described FIGS. 5-8, a hybrid approach using both work rate- and heart rate-based METs calculations can yield a more accurate METs calculation for situations when the load is unmeasurable.

Referring to step 902, the start of an exercise session is determined. In some embodiments, the start of the exercise session is determined by the processor of the fitness tracking device 100 or of the companion device 300. The start of the exercise session can be triggered by a user, or detected by either the fitness tracking device 100 or the companion device 300.

Referring to step 904, heart rate (HR) data and work rate (WR) data is received. The heart rate data and work rate data can include time stamped HR values and time stamped WR values. In some embodiments, time-stamped WR values refer to serial measurements of speed, power, or effort exerted as part of an aerobic activity. That is, in some embodiments, work rate refers to a measurement of the physical work done as a result of the exercise. As described above, the received heart rate data can be used to calculate FHR. HR and WR data is received for at least a predetermined amount of time or periods of time. For example, the fitness tracking device can be programmed to collect three periods of one minute intervals before moving to the next step. The sampling rate can be adapted for protocol being performed such as interval training. In some embodiments, the rate is at a Nyquist rate or larger to account for change in load. Workouts entailing more rapid load changes can require larger sampling frequency, while more steady state workouts can accommodate lower sampling rates. In some embodiments, the sampling rates are chosen to be 2.56 s for the work rate and 5 s (interpolated to 2.56 s) for heart rate.

Referring to step 906, the fitness tracking device 100 can determine whether a HR confidence parameter is less than 0.7. HR confidence parameter (HR conf) is a quality indicator obtained from the heart rate estimation algorithm. It is a scalar value in the range 0-1.0, larger values indicating more confident estimates of heart rate. A threshold of 0.7 was chosen to ensure optimal quality and availability of heart rate samples. Higher thresholds could lead to fewer samples. If so, the fitness tracking device 100 calculates a METs value based off the measured work rate 908. If not, the fitness tracking device 100 proceeds to the next step.

Referring to step 910, the fitness tracking device 100 determines whether a user is running and whether the user's FHR is greater than 0.4 or a different parameter tuned to the fitness level of the population. In some embodiments, the fitness tracking device 100 can determine a user is running using the motion sensing module 220 or based on a parameter entered by a user. If the user is running and the user's FHR is greater than 0.4, the fitness tracking device 100 calculates a METs value based off the measured work rate 912. If not, the fitness tracking device 100 proceeds to the next step.

Referring to step 914, the fitness tracking device 100 determines whether a user is walking and whether the user's HR-based METs is greater than 12 or a threshold chosen based on the subject's fitness level. If the user is walking and the user's HR-based METs is greater than 12, the fitness tracking device 100 calculates a METs value based off the measured work rate 916. If not, the fitness tracking device 100 uses the larger of the work rate-based METs calculation and the heart rate-based METs calculation 918.

Figure 10A:
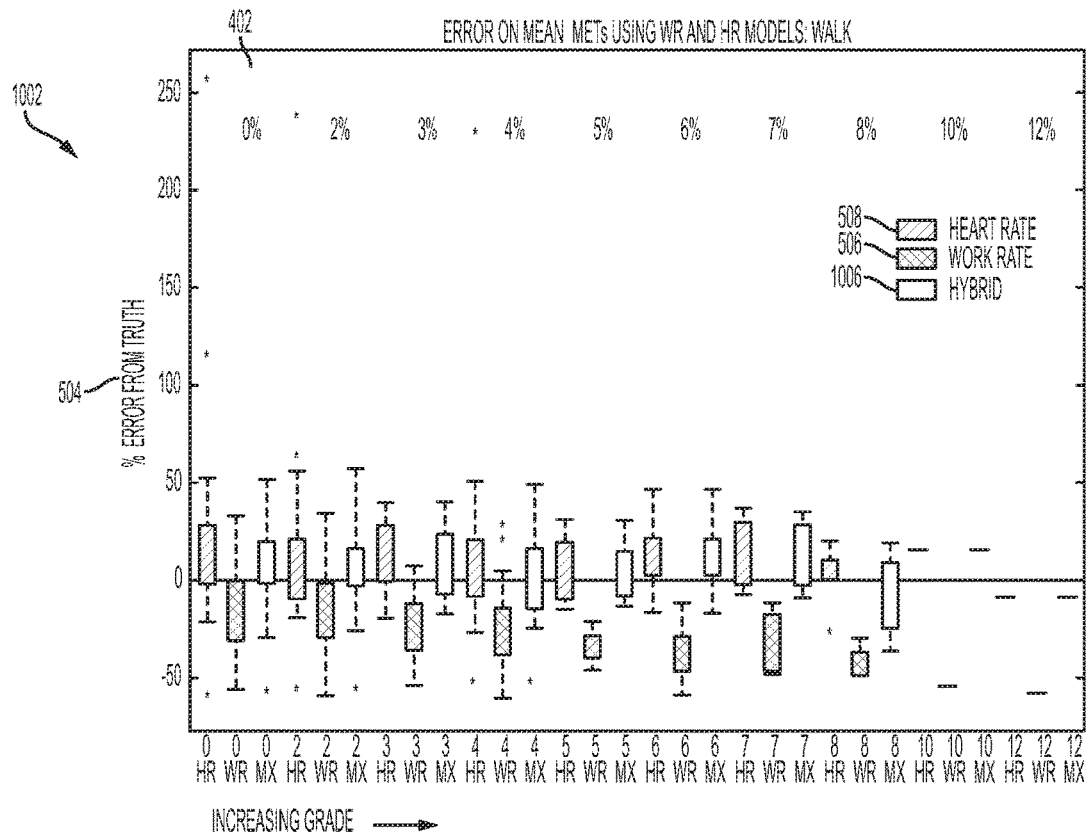
FIG. 10A is a graph 1002 showing an error on mean METs using work rate and heart rate models versus grade for 65 users participating in a walking experiment, according to some embodiments of the present disclosure.
Figure 10B:
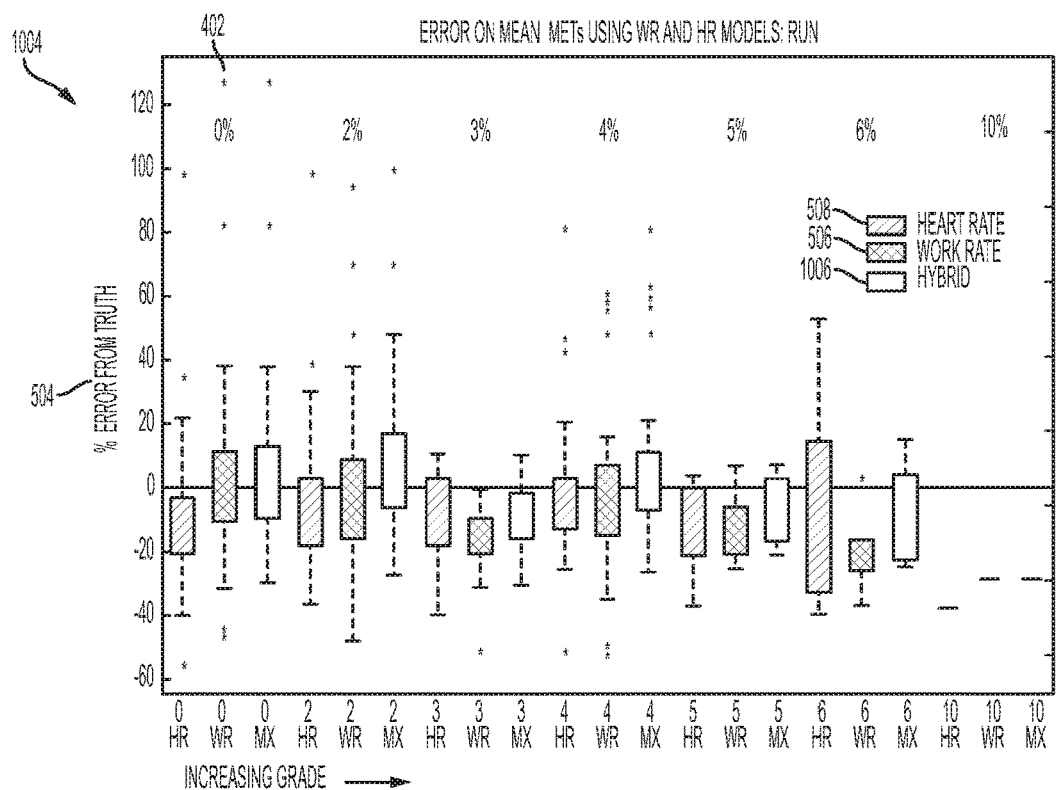
FIG. 10B is a graph 1004 showing an error on mean METs using work rate and heart rate models versus grade for 55 users participating in a running experiment, according to some embodiments of the present disclosure.

FIG. 10A is a graph 1002 showing an error on mean METs using work rate and heart rate models versus grade for 65 users participating in a walking experiment, according to some embodiments of the present disclosure. FIG. 10B is a graph 1004 showing an error on mean METs using work rate and heart rate models versus grade for 55 users participating in a running experiment, according to some embodiments of the present disclosure. Taken together, FIGS. 10A and 10B show a percentage grade 402, a percentage error from an actual number of METs expended during the experiment 504, work rate-METs range 506, heart rate-METs range 508, and a hybrid METs range 1006.

As shown in FIGS. 10A and 10B, the hybrid METs range is generally more accurate for both runners and walkers across different grades than heart rate-based METs or work rate-based METs taken individually. As such, the hybrid approach as described herein provides for a technique to calculate an unmeasurable load based on observations made about measured heart rate and work rate data.

Systems and methods are disclosed herein for determining a calorie expenditure value during an exercise session. In some embodiments, the systems and methods include determining, by a processor of a fitness tracking device, a start of an exercise session associated with a user; measuring, by at least one sensor of the fitness tracking device, heart rate values and work rate values during the exercise session; determining, by the at least one sensor of the fitness tracking device, a type of exercise associated with the exercise session, wherein the type of exercise includes running and walking; determining, by the processor of the fitness tracking device, an amount of heart rate values and work rate values being measured exceeds a threshold; calculating, by the processor of the fitness tracking device, a heart rate-calorie expenditure associated with the measured heart rate values and a work rate-calorie expenditure associated with the measured work rate values; setting, by the processor of the fitness tracking device, a hybrid calorie expenditure value for the exercise session based on a combination of the measured heart rate values, the measured work rate values, the heart rate-calorie expenditure, and the work rate-calorie expenditure, wherein the hybrid calorie expenditure value comprises: the work rate-calorie expenditure when: a HR conf is less than 0.7, the type of exercise is associated with the user running and FHR is greater than 0.4, or the type of exercise is associated with the user walking and a METs value associated with the heart rate-calorie expenditure is greater than 12; a greater expenditure value of the work rate-calorie expenditure and the heart rate-calorie expenditure when: the HR conf is greater or equal than 0.7, the type of exercise is associated with the user running and FHR is less than or equal than 0.4, and the type of exercise is associated with the user walking and a METs value associated with the heart rate-calorie expenditure is less than or equal to 12.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A method for determining an energy expenditure of a user with a wearable device, the method comprising:
    determining, by a processor circuit of the wearable device, a start of an exercise session for the user;
    detecting, by the processor circuit, an exercise type associated with the exercise session wherein the exercise type is walking or running;
    measuring, by a heart rate sensing module of the wearable device, heart rate data of the user, wherein the heart rate sensing module comprises a photoplethysmogram (PPG) sensor and the PPG sensor is configured to be worn adjacent to the user's skin;
    applying, by the processor circuit, a first time stamp to the measured heart rate data;
    collecting, by one or more work rate sensing modules of the wearable device, work rate data of the user;
    applying, by the processor circuit, a second time stamp to the collected work rate data;
    calculating, by the processor circuit, a heart rate-based energy expenditure based on the heart rate data measured at the first time stamp;
    calculating, by the processor circuit, a work rate-based energy expenditure based on the work rate data collected at the second time stamp;
    determining, by the processor circuit, an energy expenditure of the user based on the calculated heart rate-based energy expenditure and the calculated work rate-based energy expenditure; and
    outputting the energy expenditure of the user.

2. The method of claim 1, wherein calculating the heart rate-based energy expenditure comprises:
    measuring, by the heart rate sensing module, a maximum heart rate and a resting heart rate;
    determining, by the processor circuit, a heart rate confidence parameter based on the measured heart rate data;
    calculating, by the processor circuit, a fraction of heart rate reserve (FHR) based on the measured heart rate data, the maximum heart rate, and the resting heart rate; and
    calculating, by the processor circuit, the heart rate-based energy expenditure based on the FHR.

3. The method of claim 2, wherein determining the energy expenditure of the user comprises:
    determining the energy expenditure of the user as the calculated work rate-based energy expenditure when:
        the determined heart rate confidence parameter is less than a pre-defined heart rate confidence threshold,
        the detected exercise type is running and the calculated fraction of heart rate reserve is greater than a pre-defined fraction of heart rate reserve threshold, or
        the detected exercise type is walking and a heart rate-based metabolic equivalents of task is greater than a pre-defined metabolic equivalents of task threshold; and
    determining the energy expenditure of the user as the greater of the calculated heart rate-based energy expenditure and the calculated work rate-based energy expenditure when:
        the determined heart rate confidence parameter is greater than or equal to a pre-defined heart rate confidence threshold, the detected exercise type is running and the calculated fraction of heart rate reserve is less than or equal to a pre-defined fraction of heart rate reserve threshold, or the detected exercise type is walking and a heart rate-based metabolic equivalents of task is less than or equal to a pre-defined metabolic equivalents of task threshold.

4. The method of claim 3, wherein the pre-defined metabolic equivalents of task threshold is between 0 and 50.

5. The method of claim 1, wherein determining the start of the exercise session comprises determining the start of the exercise session in response to receiving an input from the user.

6. The method of claim 1, wherein the one or more work rate sensing modules comprises a motion sensing module.

7. The method of claim 6, wherein the motion sensing module comprises at least one of an accelerometer, a gyroscope, a magnetometer, an altimeter, a barometer, or a GPS sensor.

8. A system for determining an energy expenditure of a user with a wearable device, the system comprising:
a heart rate sensing module configured to measure heart rate data of the user, wherein the heart rate sensing module comprises a photoplethysmogram (PPG) sensor and the PPG sensor is configured to be worn adjacent to the user's skin;
one or more work rate sensing modules configured to collect work rate data of the user; and
a processor circuit in communication with the heart rate sensing module and the one or more work rate sensing modules and configured to execute instructions causing the processor circuit to:
determine a start of an exercise session for the user;
detect an exercise type associated with the exercise session, wherein the exercise type is walking or running;
apply a first time stamp to the measured heart rate data;
apple a second time stamp to the collected work rate data;
calculate a heart rate-based energy expenditure based on the heart rate data measured at the first time stamp;
calculate a work rate-based energy expenditure based on the work rate data collected at the second time stamp;
determine an energy expenditure of the user based on the calculated heart rate-based energy expenditure and the calculated work rate-based energy expenditure; and
output the energy expenditure of the user.

9. The system of claim 8, wherein the heart rate sensing module is configured to measure a maximum heart rate and a resting heart rate, and the instructions further cause the processor circuit to:
determine a heart rate confidence parameter based on the collected heart rate data;
calculate a fraction of heart rate reserve (FHR) based on the collected heart rate data, the maximum heart rate, and the resting heart rate; and
calculate a heart rate-based energy expenditure based on the FHR.

10. The system of claim 8, wherein the instructions further cause the processor circuit to:

determine the energy expenditure of the user as the calculated work rate-based energy expenditure when:
the determined heart rate confidence parameter is less than a pre-defined heart rate confidence threshold,
the detected exercise type is running and the calculated fraction of heart rate reserve is greater than a pre-defined fraction of heart rate reserve, or
the detected exercise type is walking and a heart rate-based metabolic equivalents of task is greater than a pre-defined metabolic equivalents of task threshold; and
determine the energy expenditure of the user as the greater of the calculated heart rate-based energy expenditure and the calculated work rate-based energy expenditure when:
the determined heart rate confidence parameter is greater than or equal to a pre-defined heart rate confidence threshold,
the detected exercise type is running and the calculated fraction of heart rate reserve is less than or equal to a pre-defined fraction of heart rate reserve, or
the detected exercise type is walking and a heart rate-based metabolic equivalents of task is less than or equal to a pre-defined metabolic equivalents of task threshold.

11. The system of claim 10, wherein the pre-defined metabolic equivalents of task threshold is between 0 and 50.

12. The system of claim 8, wherein the one or more work rate sensing modules comprises a motion sensing module.

13. The system of claim 12, wherein the motion sensing module comprises at least one of an accelerometer, a gyroscope, a magnetometer, an altimeter, a barometer, or a GPS sensor.

14. A mobile device comprising:
a wearable case;
a heart rate sensing module disposed in the wearable case and configured to measure heart rate data of the user, wherein the heart rate sensing module comprises a photoplethysmogram (PPG) sensor and the PPG sensor is configured to be worn adjacent to the user's skin;
one or more work rate sensing modules configured to collect work rate data of the user; and
a processor circuit in communication with the heart rate sensing module and the one or more work rate sensing modules and configured to execute instructions causing the processor circuit to:
determine a start of an exercise session for the user;
detect an exercise type associated with the exercise session, wherein the exercise type is walking or running;
apply a first time stamp to the measured heart rate data;
apple a second time stamp to the collected work rate data;
calculate a heart rate-based energy expenditure based on the heart rate data measured at the first time stamp;
calculate a work rate-based energy expenditure based on the work rate data collected at the second time stamp;
determine an energy expenditure of the user based on the calculated heart rate-based energy expenditure and the calculated work rate-based energy expenditure; and
output the energy expenditure of the user.

* * * * *